(12) United States Patent
Spengler et al.

(10) Patent No.: US 10,315,137 B2
(45) Date of Patent: Jun. 11, 2019

(54) SENSING SYSTEM FOR DETECTING MACHINE FLUID DEGRADATION

(71) Applicant: Caterpillar Inc., Peoria, IL (US)

(72) Inventors: Philip C. Spengler, Washington, IL (US); Jeffrey R. Ries, Metamora, IL (US); Hind Abi-Akar, Peoria, IL (US)

(73) Assignee: Caterpillar Inc., Deerfield, IL (US)

( * ) Notice: Subject to any disclaimer, the term of this patent is extended or adjusted under 35 U.S.C. 154(b) by 153 days.

(21) Appl. No.: 15/355,576

(22) Filed: Nov. 18, 2016

(65) Prior Publication Data

US 2018/0140978 A1    May 24, 2018

(51) Int. Cl.
| | |
|---|---|
| *B01D 35/143* | (2006.01) |
| *G01N 33/28* | (2006.01) |
| *B01D 35/14* | (2006.01) |
| *G01N 27/00* | (2006.01) |
| *F01M 11/10* | (2006.01) |
| *G01F 23/22* | (2006.01) |
| *G01N 17/00* | (2006.01) |

(52) U.S. Cl.
CPC ....... *B01D 35/143* (2013.01); *G01N 33/2876* (2013.01); *B01D 2201/52* (2013.01); *B01D 2201/56* (2013.01); *F01M 11/10* (2013.01); *F01M 2011/1406* (2013.01); *F16N 2200/08* (2013.01); *F16N 2260/18* (2013.01); *G01F 23/223* (2013.01); *G01N 17/00* (2013.01)

(58) Field of Classification Search
CPC ............ B01D 2201/52; B01D 2201/00; B01D 35/143; B01D 35/14; B01D 35/00; G01N 27/00; F01M 11/10; F01M 11/00

USPC ................. 422/50, 62, 68.1, 82.01
See application file for complete search history.

(56) References Cited

U.S. PATENT DOCUMENTS

| | | | |
|---|---|---|---|
| 4,675,662 A * | 6/1987 | Kondo ................ | G01N 17/00 |
| | | | 324/698 |
| 4,706,193 A | 11/1987 | Imajo et al. | |
| 7,043,402 B2 | 5/2006 | Phillips et al. | |
| 7,219,536 B2 | 5/2007 | Honeywell | |

(Continued)

FOREIGN PATENT DOCUMENTS

| | | |
|---|---|---|
| CA | 2358787 A1 | 5/2002 |
| DE | 3013740 A1 | 10/1981 |

(Continued)

OTHER PUBLICATIONS

Jim Fitch; "Determining Proper Oil and Filter Change Intervals: Can Onboard Automotive Sensors Help?" website; http://www.machinerylubrication.com/Articles/Print/562.

*Primary Examiner* — Christine T Mui
(74) *Attorney, Agent, or Firm* — Miller, Matthias & Hull (57) ABSTRACT

A sensing system for detecting degradation of a machine fluid is disclosed. The sensing system may comprise a tag having electrical contacts. The tag may be configured to transmit a wireless signal when the electrical contacts are in electrical communication. The sensing system may further comprise a dissolvable element separating the electrical contacts and obstructing electrical communication between the electrical contacts. The dissolvable element may be configured to dissolve and allow electrical communication between the electrical contacts when an acid content of the machine fluid reaches a level indicative of the degradation of the machine fluid.

9 Claims, 6 Drawing Sheets

(56) References Cited

U.S. PATENT DOCUMENTS

| | | | |
|---|---|---|---|
| 7,612,325 B1 * | 11/2009 | Watkins, Jr. | G01N 27/12 |
| | | | 250/221 |
| 8,040,243 B2 | 10/2011 | Bommer et al. | |
| 8,400,171 B2 | 3/2013 | Pena et al. | |
| 8,618,914 B2 | 12/2013 | Bachman et al. | |
| 2002/0089338 A1 | 7/2002 | Tseng | |
| 2003/0046985 A1 | 3/2003 | Schoess | |
| 2006/0230833 A1 | 10/2006 | Liu et al. | |
| 2008/0143351 A1 | 6/2008 | Lee et al. | |
| 2009/0084171 A1 | 4/2009 | Kauffman | |
| 2011/0076484 A1 * | 3/2011 | Kawai | B01J 19/126 |
| | | | 428/328 |
| 2015/0075268 A1 | 11/2015 | Qi | |
| 2015/0361840 A1 | 12/2015 | Cummins | |
| 2016/0018381 A1 * | 1/2016 | Potyrailo | G01N 27/026 |
| | | | 324/633 |

FOREIGN PATENT DOCUMENTS

| | | |
|---|---|---|
| WO | 9924812 A1 | 5/1999 |
| WO | 0045145 | 8/2000 |
| WO | 2007051216 | 5/2007 |

* cited by examiner

SENSING SYSTEM FOR DETECTING MACHINE FLUID DEGRADATION

TECHNICAL FIELD

The present disclosure generally relates to sensing systems and, more specifically, to sensing systems for detecting the degradation of machine fluids such as engine oil, transmission fluid, hydraulic fluid, and coolant fluid.

BACKGROUND

Many machines and equipment circulate fluids that perform various functions such as lubricating moving parts, transferring heat, separating moving parts, absorbing contaminants, and powering hydraulic motors and hydraulic cylinders. Such fluids may include engine oil, transmission fluid, hydraulic fluid, and coolant fluid. For instance, engine oil and transmission fluid may lubricate moving parts such as gears and pistons, while hydraulic fluid may power hydraulic cylinders, such as those used to raise and lower an implement of an earth-moving machine. However, as the machine operates and with extended hours of machine operation, such fluids may degrade due to oxidation, thermal breakdown, and/or contamination. For example, as an engine oil degrades, the acidity of the oil may increase, leading to an increase in the viscosity of the oil and eventual formation of sludge and varnish. When the acid content of the engine oil reaches a certain level, it may signify that the engine oil has reached its useable life and needs to be replaced with fresh oil.

The machine or equipment may also include one or more filters that collect contaminants such as particles and debris that have accumulated in the fluids to protect bearing surfaces, engine liners, and/or other engine parts from wear. Although such filters may extend the period of service of the fluid, they may not be equipped to detect when the fluid has reached its useable life and needs to be replaced.

U.S. Pat. No. 7,043,402 discloses a sensing system for real-time monitoring of the quality of engine lubricating oil. In particular, the sensing system includes at least two electrodes installed on a port of a lubricating oil reservoir that monitor the quality of the lubricating oil based on impedance measurements. Other sensing systems for monitoring machine fluid quality may be complex and/or expensive to implement.

Thus, there is a need for improved sensing systems for detecting degradation of machine fluids.

SUMMARY

In accordance with one aspect of the present disclosure, a sensing system for detecting degradation of a machine fluid is disclosed. The sensing system may comprise a tag having electrical contacts, and the tag may be configured to transmit a wireless signal when the electrical contacts are in electrical communication. The sensing system may further comprise a dissolvable element separating the electrical contacts and obstructing electrical communication between the electrical contacts. The dissolvable element may be configured to at least partially dissolve and allow electrical communication between the electrical contacts when an acid content of the machine fluid reaches a level indicative of the degradation of the machine fluid. The sensing system may further comprise a remote reader configured to receive the signal from the tag. Receipt of the signal from the tag at the remote reader may indicate the degradation of the machine fluid.

In accordance with another aspect of the present disclosure, a sensing system for detecting degradation of a machine fluid is disclosed. The sensing system may comprise a filter for the machine fluid. The filter may include a housing having an inlet and an outlet, and a filter medium disposed in the housing. The sensing system may further comprise a tag disposed in the housing of the filter. The tag may have electrical contacts, and may be configured to transmit a wireless signal when the electrical contacts are in electrical communication. The sensing system may further comprise a dissolvable element separating the electrical contacts of the tag and obstructing electrical communication between the electrical contacts. The dissolvable element may be configured to at least partially dissolve and allow electrical communication between the electrical contacts when an acid content of the machine fluid reaches a level indicative of degradation of the machine fluid. In addition, the sensing system may further comprise a remote reader configured to receive the signal from the tag. Receipt of the signal from the tag at the remote reader may indicate degradation of the machine fluid.

In accordance with another aspect of the present disclosure, a method for detecting degradation of a machine fluid of a machine is disclosed. The method may comprise placing a tag in contact with the machine fluid. The tag may include electrical contacts and a dissolvable element separating the electrical contact. The dissolvable element may obstruct electrical communication between the electrical contacts. The method may further comprise allowing an acid content of the machine fluid to increase with use in the machine, and permitting the dissolvable element to at least partially dissolve when the acid content of the machine fluid reaches a level indicative of degradation of the machine fluid. The method may further comprise allowing the electrical contacts to come into electrical communication, and transmitting a wireless signal from the tag to a remote reader, wherein the signal indicates the degradation of the machine fluid.

These and other aspects and features of the present disclosure will be more readily understood when read in conjunction with the accompanying drawings.

DETAILED DESCRIPTION

Figure 1:
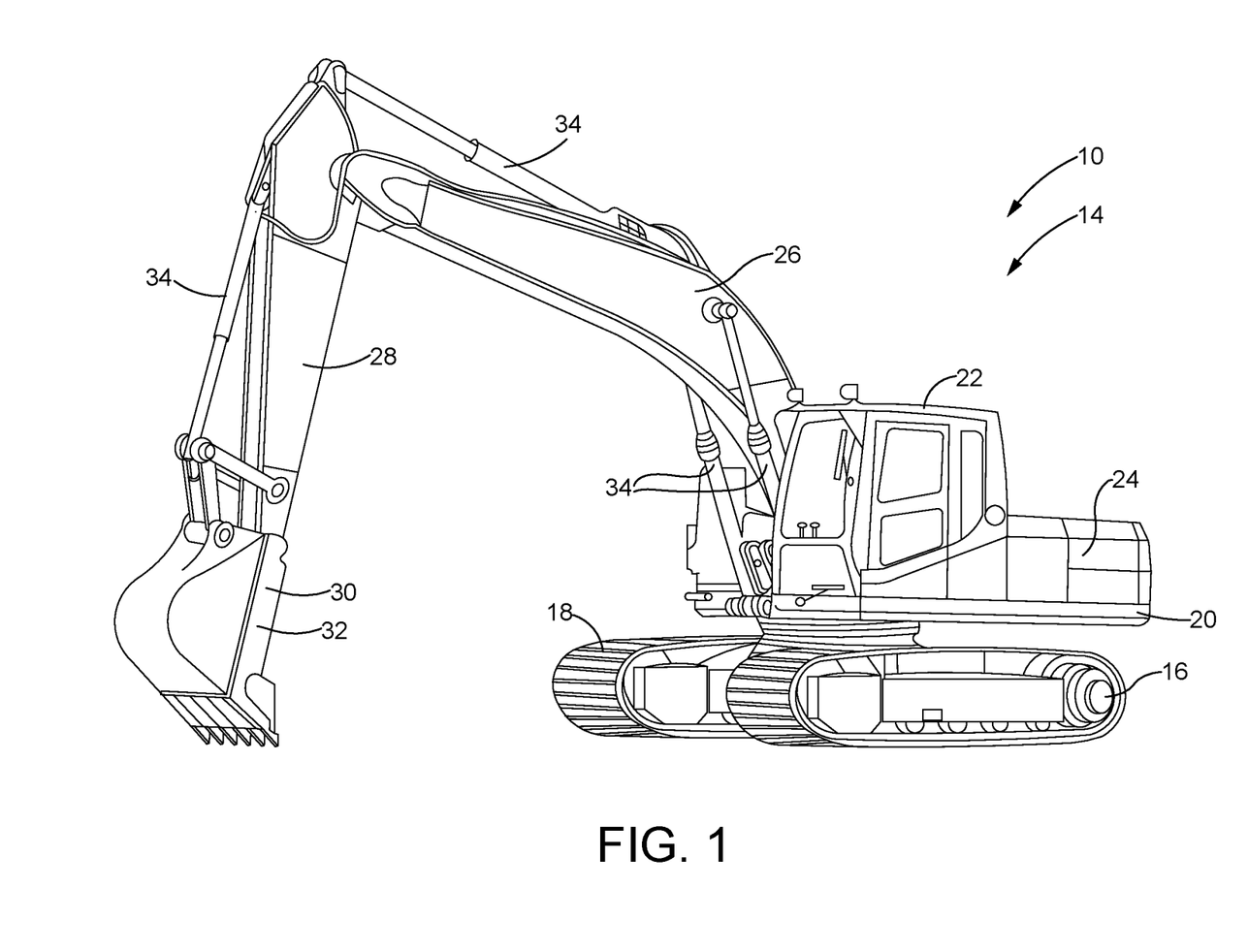
FIG. 1 is a side perspective view of a machine, constructed in accordance with the present disclosure.

Referring now to the drawings, and with specific reference to FIG. 1, a machine 10 is shown. The machine 10 may be any type of machine or equipment that circulates one or more machine fluids 12 (see FIG. 2) to perform one or more functions such as, but not limited to, lubricating moving parts or separating moving parts of the machine, actuating hydraulic cylinders, powering hydraulic motors, transferring heat, and absorbing contaminants. In this regard, a "machine fluid" as used herein may include various types of machine fluids apparent to those with ordinary skill in the art such as, but not limited to, engine oil, transmission fluid, hydraulic fluid, and coolant fluid.

As a non-limiting example, the machine 10 may be an earth-moving machine such as an excavator 14. In this example, the machine 10 may include an undercarriage 16 supporting tracks 18 (or wheels) to drive the movement of the machine 10, and a rotatable platform 20 configured for rotation with respect to the undercarriage 16. The rotatable platform 20 may support an operator cab 22, an internal combustion engine 24, and a boom 26 pivotally mounted on the rotatable platform 20. An arm 28 may be pivotally carried by the boom 26, and the arm 28 may pivotally carry an implement 30, such as a bucket 32. Adjustment of the position of the boom 26, the arm 28, and the implement 30 may be accomplished using hydraulic cylinders 34 actuated with pressurized hydraulic fluid, as will be understood by those with ordinary skill in the art. In alternative arrangements, the machine 10 may be various other types of machines such as, but not limited to, earth-moving machines or equipment, drilling machines or equipment, mining machines or equipment, automotive vehicles, and marine vehicles.

Figure 2:
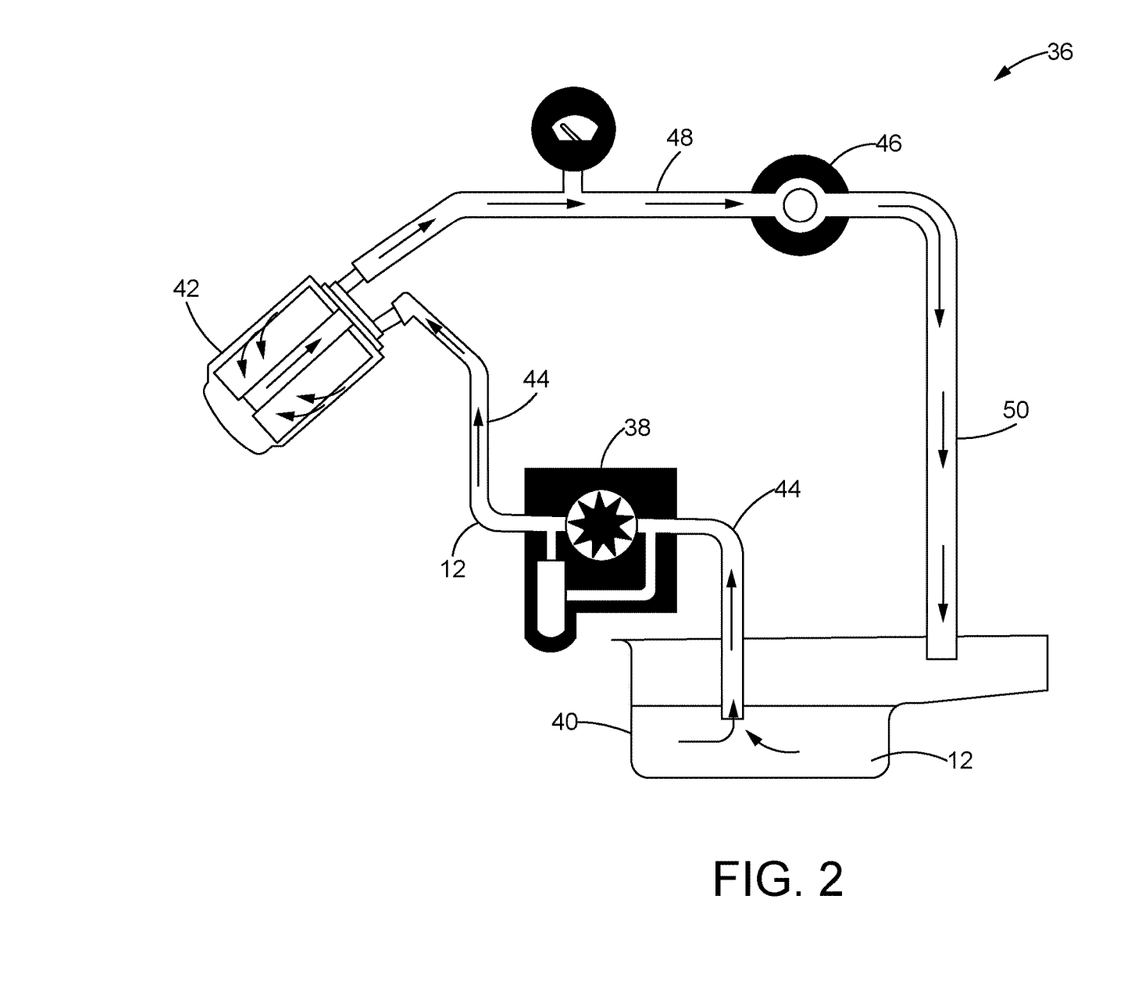
FIG. 2 is a schematic representation of a fluid circuit of a machine fluid used by the machine of FIG. 1, constructed in accordance with the present disclosure.

Turning now to FIG. 2, a fluid circuit 36 generally depicting a flow path of the machine fluid 12 though the machine 10 is shown. A pump 38 may actively drive the flow of the fluid 12 through the circuit 36. The pump 38 may draw the fluid 12 from a fluid reservoir 40 (e.g., a sump, etc.) and may drive the flow of the fluid 12 through a filter 42 via one or more conduits 44. The filter 42 may remove contaminants and particulates in the fluid 12 before the fluid 12 is directed to one or more targets 46 through one or more conduits 48. It will be understood that the target(s) 46 may vary considerably depending on the type of the machine fluid used. For instance, if the machine fluid 12 is engine oil or transmission fluid, the targets 46 may include moving parts of the machine 10 such as the transmission gears or the engine pistons for lubrication thereof. Alternatively, if the machine fluid 12 is hydraulic fluid, the targets 46 may include hydraulic motors and/or the hydraulic cylinders 34 that adjust the position of the implement 30 (or the boom 26, the arm 28, etc.) of the machine 10. After reaching the target(s) 46, the machine fluid 12 may be cycled back to the reservoir 40 through one or more conduits 50, allowing the process to repeat. Those with ordinary skill in the art will understand that the flow circuit 36 of FIG. 2 may be considerably more complex in practice and may include additional components such as valves, additional pumps, and/or pressure gauges, among other components. In other arrangements, the pump 38 may be downstream of the filter 42, or the flow of the fluid 12 through the circuit 36 may occur passively without the use of a pump.

Figure 3:
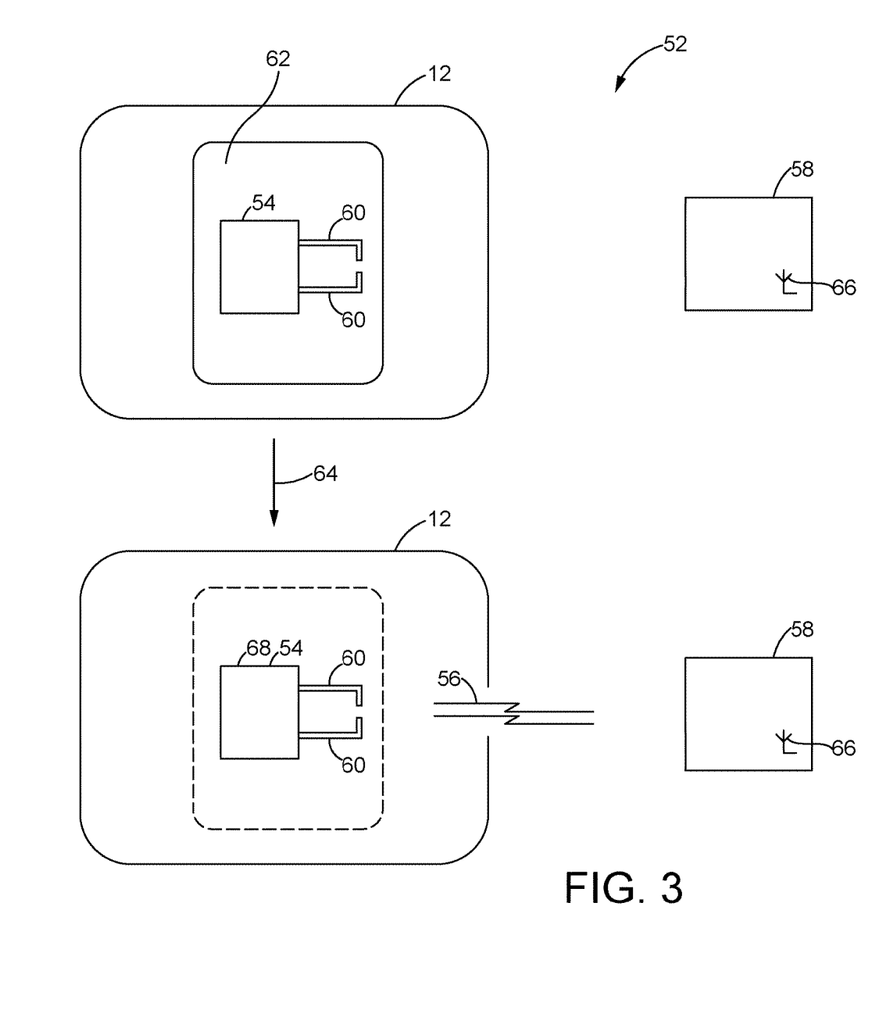
FIG. 3 is a schematic representation of a sensing system for detecting degradation of the machine fluid having a tag encapsulated in a dissolvable element, constructed in accordance with the present disclosure.

Referring to FIG. 3, a sensing system 52 for detecting the degradation of the machine fluid 12 is shown. Degradation of the machine fluid 12 may occur when the quality of the machine fluid 12 has decreased to a level that requires the replacement of the machine fluid 12 with fresh fluid. More specifically, the degradation of the machine fluid 12 may occur when the acid content of the machine fluid 12 increases to a level characteristic of degradation of the fluid. Thus, it will be understood that the acid content at which degradation of the machine fluid 12 occurs may vary considerably depending on the type of the machine fluid 12 used.

The sensing system 52 may include a tag 54 that is configured to transmit a signal 56 to a remote reader 58 when the acid content of the machine fluid 12 reaches a level indicative of degradation of the machine fluid 12. The signal 56 may be a wireless signal, such as a wireless radio-frequency (RF) signal. For instance, the tag 54 may be a radio-frequency (RF) tag. The tag 54 may include two or more electrical contacts 60 that come into electrical communication and permit transmission of the signal 56 to the remote reader 58 when the machine fluid 12 degrades. The tag 54 may be surrounded or encapsulated by a dissolvable element 62 that separates the electrical contacts 60 and obstructs electrical communication between the contacts 60 prior to degradation of the fluid 12.

As shown in FIG. 3, the tag 54 encapsulated in the dissolvable element 62 may be placed in contact with the machine fluid 12 during use. As the machine fluid 12 ages and begins to degrade 64, the acid content in the machine fluid 12 may increase. The increased acidity of the machine fluid 12 may cause the dissolvable element 62 to at least partially dissolve, allowing the machine fluid 12 to flow between the electrical contacts 60 and permit electrical communication between the contacts 60. When in electrical communication, the electrical contacts 60 may complete the circuit of the tag 52, enabling the transmission of the signal 56 to the remote reader 58. An antenna 66 of the remote reader 58 may capture the signal 56 transmitted by the tag 54, thereby providing a positive indicator of machine fluid degradation at the remote reader 58.

The remote reader 58 may be associated with a hand-held device that enables an operator or technician to monitor the degradation of the machine fluid 12 remotely. In other arrangements, the remote reader 58 may be associated with or may communicate with a remote operator interface such as a computer or internet-enabled device to allow an operator or technician to track the quality of the machine fluid 12 from a remote work station. As yet another alternative, the remote reader 58 may be associated with or may communicate with an operator interface of the machine 10, such as a computer or display in the operator cab 22. In any event, receipt of the signal 56 at the remote reader 58 may inform the operator or technician that the machine fluid 12 has degraded and needs to be replaced with fresh fluid.

The tag 54 may be a chip 68 configured to transmit the wireless signal 56 when the contacts 60 are in electrical communication. For example, the tag 54 may be a radio-frequency identification (RFID) chip that transmits an RF signal in a frequency range compliant with RFID. For instance, the signal 56 may have a frequency in the range of about 860 to about 915 megahertz (MHz), although the frequency range may vary depending on varying standards characterizing RFID signals. In addition, the RFID chip may be passive and may be powered by the remote reader 58. In this case, the RFID chip may collect energy from the remote reader 58 and may transmit the signal 56 to the remote reader 58 when the electrical contacts 60 are in electrical communications. However, the RFID chip may also be active and may include a local power source, such as a battery.

Alternatively, the signal 56 transmitted by the tag 54 may be in a frequency range characteristic of BLUETOOTH® signals. That is, the signal 56 may have a frequency ranging from about 2.4 gigahertz (GHz) to about 2.485 GHz, but may also deviate from this range depending on varying standards characterizing BLUETOOTH® signals. Accordingly, in this arrangement, the chip 68 may be a BLUETOOTH® chip.

As yet another possibility, the signal 56 transmitted by the tag 54 may be in a frequency range characteristic of wireless fidelity (WI-FI®) signals. That is, the signal 56 may have a frequency of about 2.4 GHz, about 3.6 GHz, about 4.9 GHz, about 5 GHz, or about 5.9 GHz, but may also deviate from these frequencies depending on varying standards characterizing WI-FI® signals. In this arrangement, the chip 68 may be a WI-FI® chip.

The dissolvable element 62 may be formed from one or more compounds that is sensitive to acid and at least partially dissolves in the machine fluid 12 under acidic conditions. The chemical identity of the dissolvable element 62 may be chosen such that the dissolvable element 62 at least partially dissolves at the acid content that is characteristic of degradation of the particular machine fluid 12 used. As an illustrative example, if degradation of the machine fluid 12 is indicated at a total base number of 4, as measured by standard tests ASTM D2896, D4793 and/or equivalent tests, the chemical identity of the dissolvable element 62 may be chosen such that the dissolvable element 62 at least partially dissolves when the total base number of the machine fluid 12 reaches 4. Those with ordinary skill in the art will understand that the acid content at which the dissolvable element 62 at least partially dissolves will depend on the type of machine fluid 12 used, its acid tolerance, as well as established acid tolerance limits of the particular machine fluid. As non-limiting possibilities, the dissolvable element 62 may be formed from or may include a compound such as magnesium oxide (MgO), zinc oxide (ZnO), cadmium oxide (CdO), and combinations thereof.

The electrical contacts 60 may be formed from a conductive material that is chemically stable in the machine fluid 12. For example, the electrical contacts 60 may be formed from a ferrous material, such as iron or an iron alloy. In other arrangements, the electrical contacts 60 may be formed from other types of metals, metal alloys, or other conductive materials that are chemically stable in the machine fluid 12.

Figure 4:
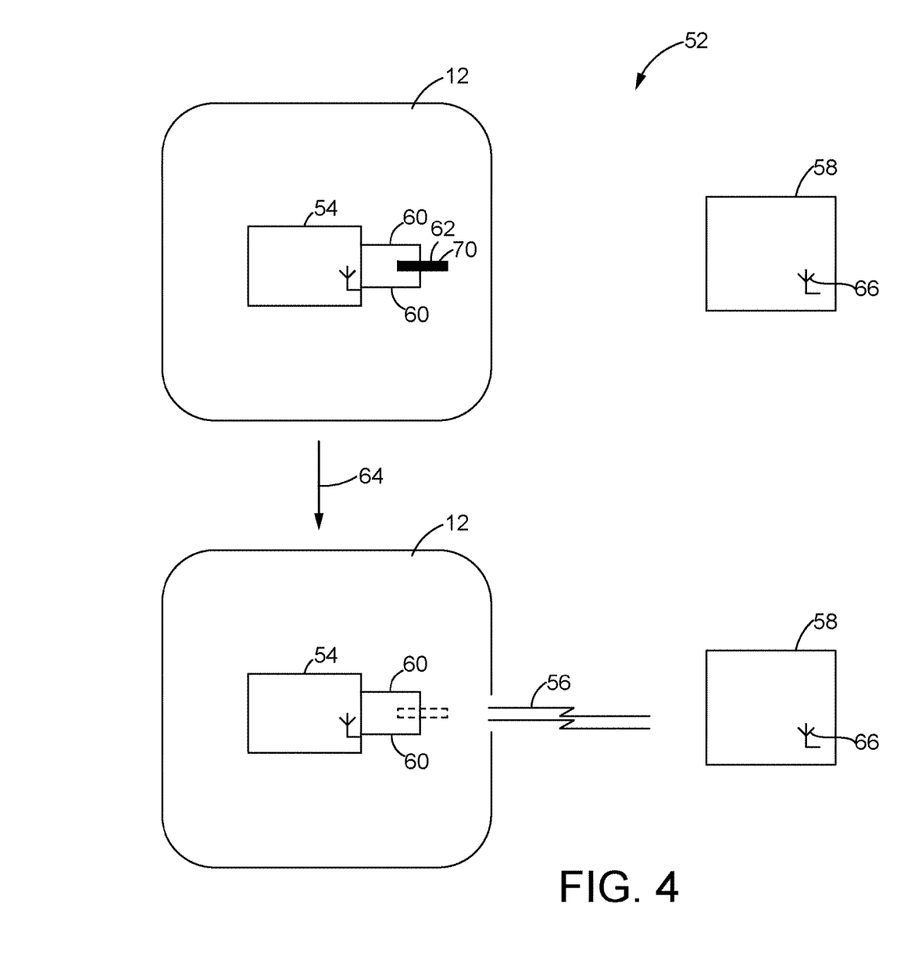
FIG. 4 is a schematic representation similar to FIG. 3 but with the dissolvable element positioned between electrical contacts of the tag, constructed in accordance with the present disclosure.

Turning to FIG. 4, an alternative design of the sensing system 52 is shown. In this arrangement, the dissolvable element 62 may be a disk-shaped structure 70 positioned between and separating the electrical contacts 60 to obstruct electrical communication therebetween. Although shown as rectangular, the disk-shaped structure 70 may have any shape insertable between the electrical contacts 60 such as, but not limited to, circular, polygonal, or amorphous shapes. As the machine fluid 12 begins to degrade 64 and the acid content of the fluid increases, the dissolvable element 62 may at least partially dissolve, allowing the contacts 60 to come into physical contact to permit electrical communication therebetween. In some arrangements, the contacts 60 may be spring-loaded to drive the contacts 60 into physical contact upon dissolution of the dissolvable element 62, as will be understood by those with ordinary skill in the art. Alternatively, the electrical contacts 60 may remain separated upon dissolution of the dissolvable element 62, and the machine fluid 12 may flow between the contacts 60 to complete the circuit and allow electrical communication between the contacts 60. In any of the above arrangements, electrical communication between the contacts 60 may allow the tag 54 to transmit the signal 56 to the remote reader 58, indicating that the machine fluid 12 has degraded.

Figure 5:
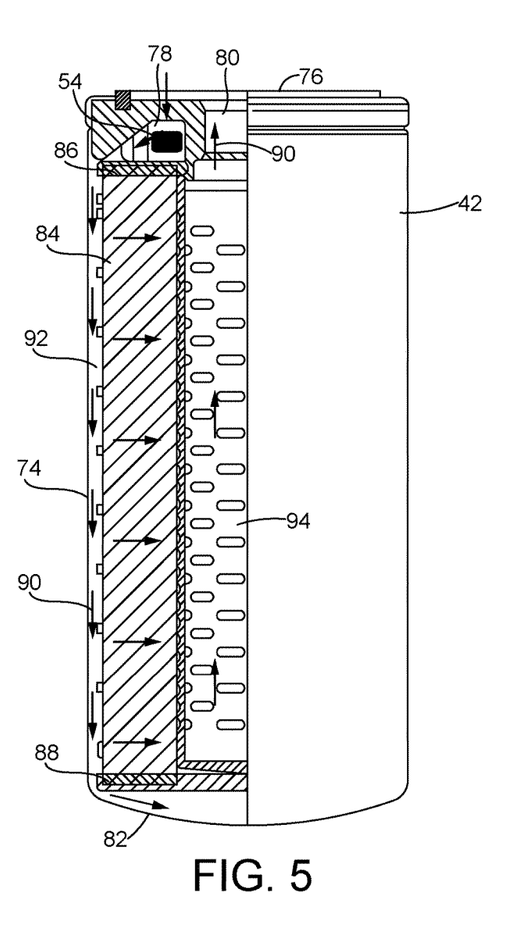
FIG. 5 is a partial cross-sectional view of a filter for the machine fluid having the tag disposed therein, constructed in accordance with the present disclosure.

As shown in FIG. 5, the tag 54 may be placed in the filter 42 for the machine fluid 12. As one possibility, the filter 42 may be a spin-on filter including a housing 74 having a top end 76 defining an inlet 78 and an outlet 80 for the machine fluid 12, a bottom end 82, and a filter medium 84 disposed in the housing 74 for trapping particulates and contaminants in the machine fluid 12. The filter medium 84 may be disposed between a top end cap 86 near the top end 76, and a bottom end cap 88 near the bottom end 82. The machine fluid 12 may follow a flow path 90 through the filter 42, as shown in FIG. 5. Specifically, the fluid 12 may enter the filter 42 through the inlet 78 at the top end 76 and subsequently flow along an outer periphery 92 of the filter 42 and through the filter medium 84 into a center tube 94 before exiting through the outlet 80 at the top end 76. Some of the fluid 12 may reach the bottom end 82 before flowing up flowing up through the center tube 94, as shown.

Figure 6:
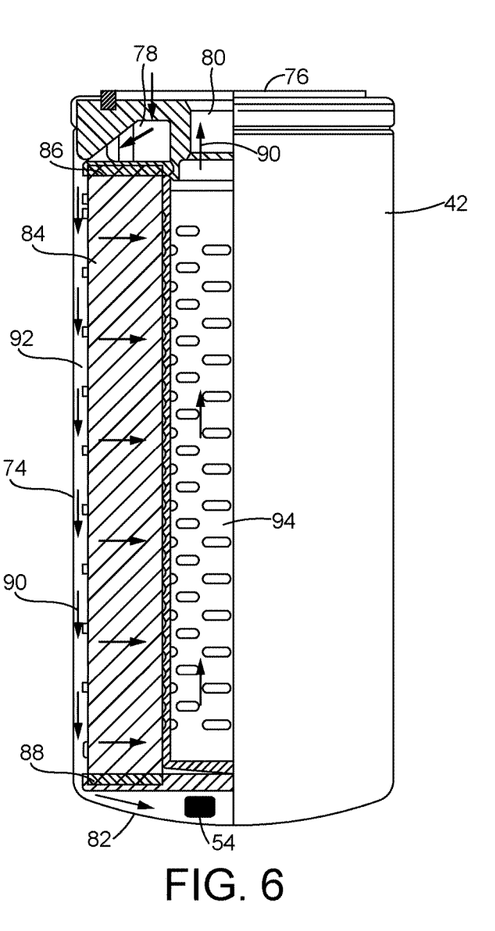
FIG. 6 is a partial cross-sectional view similar to FIG. 5, but with the sensor placed at a different location in the filter, constructed in accordance with the present disclosure.

The tag 54 may be placed on the "dirty side" of the filter 42. That is, the tag 54 may be placed on the side of the filter 42 containing the fluid 12 that has not been completely filtered through the filter medium 84. For instance, as shown in FIG. 5, the tag 54 may be placed inside the housing 74 near the inlet 78 between the top end 76 and the top end cap 86. Alternatively, as shown in FIG. 6, the tag 54 may be placed inside the housing 74 between the bottom end 82 and the bottom end cap 88. In other arrangements, the tag 54 may be placed along the outer periphery 92 of the filter 42, or on the "clean side" of the filter 42 such as in the center tube 94 or near the outlet 80. In any event, as the acid content of the machine fluid 12 flowing through the filter 42 increases to a level indicative of degradation, the tag 54 may transmit the signal 56 to the remote reader 58 to signal degradation as described above.

It will be understood that the structure of the filter 42 of FIGS. 5-6 is merely exemplary and that the filter 42 may be any type of engine oil filter, transmission fluid filter, hydraulic fluid filter, or coolant filter apparent to those with ordinary skill in the art. In such arrangements, the tag 54 may be placed on the dirty side or on the clean side of the filter at various locations. Variations such as these also fall within the scope of the present disclosure.

INDUSTRIAL APPLICABILITY

In general, the teachings of the present disclosure may find broad applicability in many industries including, but not limited to, construction, mining, agriculture, and automotive industries. More specifically, the present disclosure may find applicability in any industry using machines or equipment that circulate a machine fluid subject to degradation with extended use such as, but not limited to, engine oil, transmission fluid, hydraulic fluid, and coolant fluid.

Figure 7:
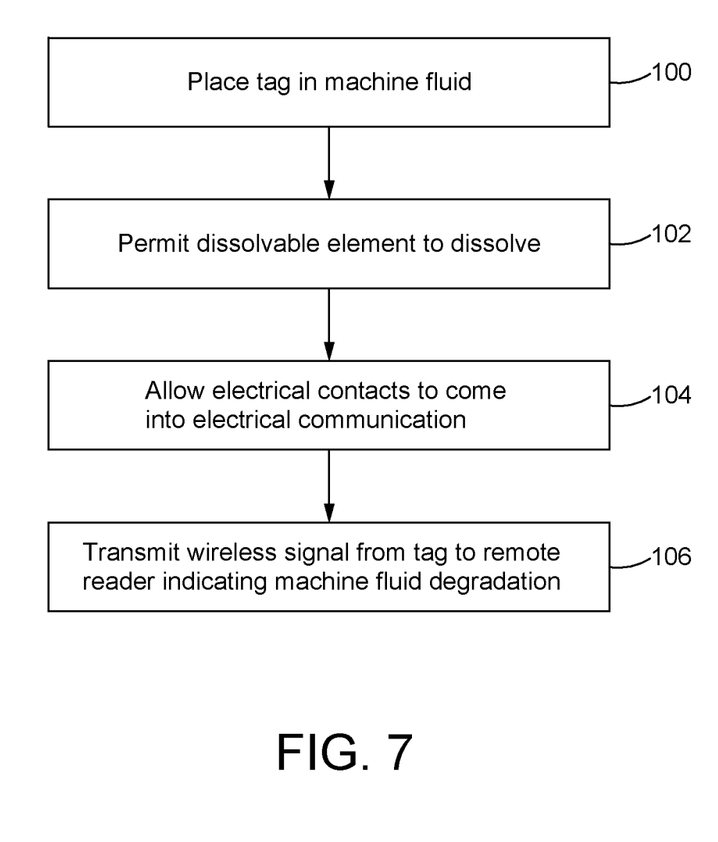
FIG. 7 is a flowchart of a series of steps involved in detecting degradation of the machine fluid using the sensing system, in accordance with a method of the present disclosure.

Referring to FIG. 7, a series of steps that may be involved in detecting degradation of the machine fluid 12 using the sensing system 52 is shown. Beginning with a first block 100, the tag 54 may be placed in contact with the machine fluid 12. For example, the tag 54 may be a pill-like structure that is placed inside of the filter 42 (see FIGS. 5-6), or at another location in the fluid circuit 36. At a next block 102, the dissolvable element 62 may be permitted to at least partially dissolve when the acid content of the machine fluid 12 increases as a result of degradation. Dissolution of the dissolvable 62 may then allow the electrical contacts 60 that were previously separated by the dissolvable element 62 to come into electrical communication (block 104). Once the electrical contacts 60 are in electrical communication, the circuit of the tag 54 may be completed, thereby permitting the tag 54 to transmit the signal 56 to the remote reader 58 indicating degradation of the machine fluid 12 (block 106).

The sensing system disclosed herein may provide a reliable tool for remotely tracking the quality of machine fluids that exhibit an increase in acid content with degradation. The sensing system includes a tag that may be placed in contact with the machine fluid during operation of the machine. As the acid content of the machine fluid increases with use, the tag may transmit a wireless signal to a remote reader to notify the operator or technician that the machine fluid needs to be replaced with fresh fluid. In some implementations, the tag may be placed on the dirty side of the filter for the machine fluid to track the quality of the fluid prior to filtering. The sensing system disclosed herein may provide a straightforward and cost-effective strategy to monitor machine fluid degradation compared to more complex and expensive detection methods of the prior art.

It is expected that the technology disclosed herein may find wide industrial applicability in a wide range of areas such as, but not limited to, construction, automotive, marine, mining, agriculture, and earth-moving equipment applications.

What is claimed is:

1. A sensing system for detecting degradation of a machine fluid, comprising:
   a tag having electrical contacts, the tag being configured to transmit a wireless signal when the electrical contacts are in electrical communication; and
   a dissolvable element between the electrical contacts and obstructing physical contact and the electrical communication between the electrical contacts, the dissolvable element being configured to at least partially dissolve when an acid content of the machine fluid reaches a level indicative of the degradation of the machine fluid, the dissolution of the dissolvable element initiating the electrical communication between the electrical contacts and the transmission of the wireless signal by allowing the electrical contacts to come into physical contact or by allowing the machine fluid to flow between the electrical contacts, the wireless signal transmitted by the tag indicating the degradation of the machine fluid.

2. The sensing system of claim 1, wherein the dissolvable element encapsulates the tag.

3. The sensing system of claim 1, wherein the dissolvable element is a disk-shaped structure positioned between the electrical contacts.

4. The sensing system of claim 1, wherein the dissolvable element is formed from a compound selected from the group consisting of magnesium oxide, zinc oxide, cadmium oxide, and combinations thereof.

5. The sensing system of claim 1, wherein the machine fluid is selected from engine oil, transmission fluid, hydraulic fluid, and coolant fluid.

6. The sensing system of claim 1, wherein the tag is a passive radio frequency identification (RFID) chip.

7. The sensing system of claim 1, wherein the signal is a radio-frequency signal having a frequency ranging between about 2.4 gigahertz to about 2.485 gigahertz.

8. The sensing system of claim 1, wherein the signal is a radio-frequency signal having a frequency of about 2.4 gigahertz, 3.6 gigahertz, 4.9 gigahertz, 5 GHz, or 5.9 gigahertz.

9. The sensing system of claim 1, further comprising a remote reader configured to receive the signal from the tag, receipt of the signal from the tag indicating the degradation of the machine fluid.

\* \* \* \* \*